US008827976B2

(12) United States Patent
Studer

(10) Patent No.: US 8,827,976 B2
(45) Date of Patent: Sep. 9, 2014

(54) SYSTEM FOR AMBULATORY DRUG INFUSION COMPRISING A FILLING APPARATUS FOR FLEXIBLE CONTAINERS, CONTAINER ASSEMBLY, AND USE OF A FLEXIBLE CONTAINER

(75) Inventor: Gerald Studer, Flaach (CH)

(73) Assignee: Roche Diagnostics International AG, Steinhausen (CH)

( * ) Notice: Subject to any disclaimer, the term of this patent is extended or adjusted under 35 U.S.C. 154(b) by 88 days.

(21) Appl. No.: 13/157,797

(22) Filed: Jun. 10, 2011

(65) Prior Publication Data

US 2012/0150139 A1   Jun. 14, 2012

Related U.S. Application Data

(63) Continuation of application No. PCT/EP2009/006998, filed on Sep. 29, 2009.

(30) Foreign Application Priority Data

Dec. 12, 2008   (EP) .................................... 08021594

(51) Int. Cl.
*A61B 19/00* (2006.01)
(52) U.S. Cl.
USPC .......................................................... 604/408
(58) Field of Classification Search
USPC .......................................................... 604/408
See application file for complete search history.

(56) References Cited

U.S. PATENT DOCUMENTS

| | | | | |
|---|---|---|---|---|
| 3,468,308 A | * | 9/1969 | Bierman | 604/141 |
| 3,469,578 A | * | 9/1969 | Bierman | 604/132 |
| 4,140,117 A | * | 2/1979 | Buckles et al. | 604/132 |
| 4,201,207 A | * | 5/1980 | Buckles et al. | 604/132 |
| 4,318,400 A | * | 3/1982 | Peery et al. | 604/18 |
| 4,337,769 A | * | 7/1982 | Olson | 604/251 |
| 4,386,929 A | * | 6/1983 | Peery et al. | 604/132 |
| 4,398,908 A | * | 8/1983 | Siposs | 604/31 |
| 4,548,607 A | * | 10/1985 | Harris | 604/891.1 |

(Continued)

FOREIGN PATENT DOCUMENTS

| | | |
|---|---|---|
| EP | 1970677 A1 | 9/2008 |
| EP | 2179755 A1 | 4/2010 |
| WO | 2008/007422 A1 | 1/2008 |

OTHER PUBLICATIONS

International Search Report, Application No. PCT/EP2009/006998, International Filing Date Sep. 29, 2009, 4 pages.

(Continued)

*Primary Examiner* — Susan Su
*Assistant Examiner* — Guy K Townsend
(74) *Attorney, Agent, or Firm* — Dinsmore & Shohl LLP

(57) ABSTRACT

An embodiment directed towards a system for ambulatory drug infusion over an extended time period from a flexible container is disclosed, and in which the system comprises a filling apparatus with a hollow support structure defining a container compartment, the container compartment being adapted to receive, fully or in part, the flexible container, and the support structure being adapted to limit the expansion of the flexible container by contacting the flexible container upon being filled, thus defining a maximum filling volume of the flexible container. In other embodiments, a container assembly is disclosed that comprises a flexible container and a support structure as well as use of a flexible container in or in combination with a system according to the invention or a container assembly according to the invention.

20 Claims, 8 Drawing Sheets

(56) References Cited

U.S. PATENT DOCUMENTS

| | | | | | |
|---|---|---|---|---|---|
| 4,551,133 | A | * | 11/1985 | Zegers de Beyl et al. | 604/66 |
| 4,559,038 | A | * | 12/1985 | Berg et al. | 604/153 |
| 4,588,394 | A | * | 5/1986 | Schulte et al. | 604/9 |
| 4,601,707 | A | * | 7/1986 | Albisser et al. | 604/131 |
| 4,626,244 | A | * | 12/1986 | Reinicke | 604/141 |
| 4,634,427 | A | * | 1/1987 | Hannula et al. | 604/288.02 |
| 4,658,990 | A | | 4/1987 | Ramage | |
| 4,668,231 | A | * | 5/1987 | de Vries et al. | 604/891.1 |
| 4,681,560 | A | * | 7/1987 | Schulte et al. | 604/9 |
| 4,699,615 | A | * | 10/1987 | Fischell et al. | 604/131 |
| 4,702,397 | A | * | 10/1987 | Gortz | 222/211 |
| 4,741,733 | A | * | 5/1988 | Winchell et al. | 604/514 |
| 4,828,551 | A | * | 5/1989 | Gertler et al. | 604/208 |
| 4,898,584 | A | * | 2/1990 | Borsanyi et al. | 604/153 |
| 4,898,585 | A | * | 2/1990 | Borsanyi et al. | 604/153 |
| 4,909,790 | A | * | 3/1990 | Tsujikawa et al. | 604/132 |
| 5,011,477 | A | * | 4/1991 | Winchell et al. | 604/132 |
| 5,098,409 | A | * | 3/1992 | Stock | 604/246 |
| 5,105,983 | A | | 4/1992 | Sancoff et al. | |
| 5,211,632 | A | * | 5/1993 | Tsukada | 604/132 |
| 5,298,025 | A | * | 3/1994 | Hessel et al. | 604/118 |
| 5,306,257 | A | * | 4/1994 | Zdeb | 604/131 |
| 5,514,096 | A | * | 5/1996 | Hiejima | 604/132 |
| 5,697,919 | A | * | 12/1997 | Kinoshita et al. | 604/248 |
| 5,700,244 | A | * | 12/1997 | Kriesel | 604/132 |
| 5,776,103 | A | * | 7/1998 | Kriesel et al. | 604/132 |
| 5,906,597 | A | * | 5/1999 | McPhee | 604/246 |
| 5,957,895 | A | * | 9/1999 | Sage et al. | 604/181 |
| 6,074,369 | A | * | 6/2000 | Sage et al. | 604/181 |
| 6,171,298 | B1 | * | 1/2001 | Matsuura et al. | 604/891.1 |
| 6,183,461 | B1 | * | 2/2001 | Matsuura et al. | 604/502 |
| 6,312,411 | B1 | * | 11/2001 | Kanai | 604/153 |
| 6,315,769 | B1 | * | 11/2001 | Peer et al. | 604/891.1 |
| 6,516,950 | B1 | * | 2/2003 | Robertson | 206/539 |
| 6,802,823 | B2 | * | 10/2004 | Mason | 604/141 |
| 7,214,221 | B2 | * | 5/2007 | Fentress et al. | 604/890.1 |
| 7,250,037 | B2 | * | 7/2007 | Shermer et al. | 604/134 |
| 7,309,333 | B2 | * | 12/2007 | Mason | 604/500 |
| 8,286,484 | B2 | * | 10/2012 | Studer | 73/304 R |
| 2002/0120236 | A1 | * | 8/2002 | Diaz et al. | 604/151 |
| 2007/0293817 | A1 | * | 12/2007 | Feng et al. | 604/65 |
| 2009/0247950 | A1 | * | 10/2009 | Tsukada et al. | 604/132 |
| 2011/0107853 | A1 | * | 5/2011 | Studer | 73/862.381 |
| 2011/0108158 | A1 | * | 5/2011 | Huwiler et al. | 141/2 |

OTHER PUBLICATIONS

Written Opinion, Application No. PCT/EP2009/006998, International Filing Date Sep. 29, 2009, 6 pages.

* cited by examiner

SYSTEM FOR AMBULATORY DRUG INFUSION COMPRISING A FILLING APPARATUS FOR FLEXIBLE CONTAINERS, CONTAINER ASSEMBLY, AND USE OF A FLEXIBLE CONTAINER

CROSS REFERENCE TO RELATED APPLICATIONS

This application is a continuation application of International Application No. PCT/EP2009/006998, filed 29 Sep. 2009, which claims the priority from European Patent Application No. 08021594.0, filed 12 Dec. 2008.

TECHNICAL FIELD

The present disclosure discusses embodiments of the invention related to a system for ambulatory drug infusion, the use of a flexible container in such a system as well as a container assembly.

BACKGROUND

Ambulatory infusion apparatuses are known in the art for a variety of applications. In particular, ambulatory infusion apparatuses adapted for insulin administration form a basis for a state-of-the-art therapy of diabetes mellitus by CSII (Continuous Subcutaneous Insulin Infusion). Those devices are typically computer controlled micro dosing pumps which are adapted to be worn continuously and concealed from view. Such insulin dosing pumps are manufactured, e.g., by Disetronic Medical Systems, AG, Switzerland, and are commercially available as Accu-Chek® Spirit. Those devices are of the syringe-driver type and comprise a typically cylindrical drug cartridge out of which insulin is forced into an infusion line by displacing a cartridge plunger in a controlled manner.

For a variety of technical as well as convenience and application-related reasons, recent systems are based on a different fluidic architecture, for example according to the disclosure of the European patent application EP 1970677A1. For such and some further designs, a drug cartridge as known from state-of-the-art systems is less favorable and may therefore be replaced by a flexible container. Such flexible containers are typically made of two, for example, circular or rectangular sheets of an elastic foil, in which the sheets are bonded in a circumferential area. Further design aspects and materials for such flexible containers are disclosed, among others, in the co-pending European patent application 08167548.0. For illustrative purposes, FIG. 1 shows a flexible container of this type in its filled state. The flexible container 20 is made of two elastic foil sheets 21, 21a which form a container body and comprises a fluidic connector 30. Variations of the design without changing the overall operation principle are obvious for a person skilled in the art. For example, instead of two separate sheets, one folded sheet may be used for the container body. In a further variant, the container body may be partly rigid and be made, for example tank-like and have a cover or top made from a flexible foil sheet. The embodiments of the present invention may be used in connection with all of those designs.

It is to be appreciated that a flexible container made of two elastic foil sheets may be substantially flat in its empty state and assume a 'cushion-like' shape upon being filled. The main direction of expansion is substantially normal to a plane which is defined by the empty container. The expansion is associated with a strain of the foil sheets which increases with the filling volume.

When the drug reservoir of an ambulatory infusion apparatus is filled by a patient, costs and convenience are major issues. Particular problems result from the fact that ambulatory infusion devices are typically operated by the patient himself or herself, i.e., a person without special skills in the fields of medicine or medical technology. In many cases, diabetes is accompanied by further diseases or handicaps such as severe ametropia and/or tactile distortions. Therefore, simple handling is of utmost importance. The drug containers are typically single-use items and are designed to hold the drug amount of one week or less. The process of filling and replacing the drug container accordingly has to be carried out quite often by the patient.

Furthermore, it has to be understood that drug containers are often not filled to the maximum amount. The patient typically fills the drug container to a volume in dependence of his or her individual insulin demand as well as the maximum storing time in the container which is limited. Especially when stored in a container made of plastics or plastic foils, drugs such as insulin formulations are known to be stable for a limited time only before they substantially degrade. In addition to time, the environmental temperature is known to have impact on the degradation. Therefore, diabetics needing comparatively little insulin per time period, such as children, as well as patients living in zones of high temperature, often do not fill the drug container to the maximum specified filling volume.

In contrast to a syringe-like drug container, filling beyond the specified maximum filling volume is well possible for a flexible container. Overfilling results in an increased leakage danger and may prevent the flexible container from smoothly fitting into a corresponding container compartment of the infusion apparatus.

During application of a drug container in an ambulatory infusion apparatus, monitoring of the drug amount remaining in the container is required in order to alert the user in due time before the reservoir is empty. For a cylindrical cartridge having a displaceable plug, the plug position within the cartridge is proportional with the filling volume. By determining the plug position or the plug displacement with respect to an initial reference position, the remaining drug volume may accordingly be obtained. In contrast to this, such a simple geometric measure is not available for flexible containers for alarming the user about the container becoming empty. It is therefore desirable to fill those containers to a well defined initial filling volume, such that the remaining drug volume can be computed from the initial drug volume and the drug volume already administered.

SUMMARY

In one embodiment, a system for ambulatory drug infusion over an extended time period is disclosed. The system may comprise an ambulatory infusion apparatus, in which the infusion apparatus comprises a flexible container or a container coupler for fluidically coupling a flexible container, a dosing unit in fluidic connection with the flexible container or a dosing unit coupler for fluidically coupling the flexible container and a dosing unit, and an electronic controller unit configured to control operation of the dosing unit. The system may further comprise a filling apparatus for the flexible container, in which the filling apparatus comprises a hollow support structure defining a container compartment, the container compartment being adapted to receive, fully or in part, the flexible container, and the support structure being adapted to limit the expansion of the flexible container by contacting the flexible container upon being filled, thus defining a maximum filling volume of the flexible container.

In another embodiment, a container assembly is disclosed and in which the container assembly may comprises a flexible container, the flexible container comprising a container body at least one wall of which is made by a sheet of an elastic foil and a fluidic connector for fluidically connecting the container, the flexible container expanding upon being filled; and a hollow support structure defining a container compartment, the flexible container being, at least in part, arranged in the container compartment, the support structure being adapted to limit the expansion of the flexible container by contacting the flexible container upon being filled, thus defining a maximum filling volume of the flexible container.

In still another embodiment, a method of preventing overfilling a flexible container with a defined drug amount comprising utilizing the flexible container in or in combination with a system according to an embodiment of the invention.

In yet another embodiment, a method of preventing overfilling a flexible container with a defined drug amount comprising utilizing the flexible container in a container assembly according to an embodiment of the invention.

Figure 1:
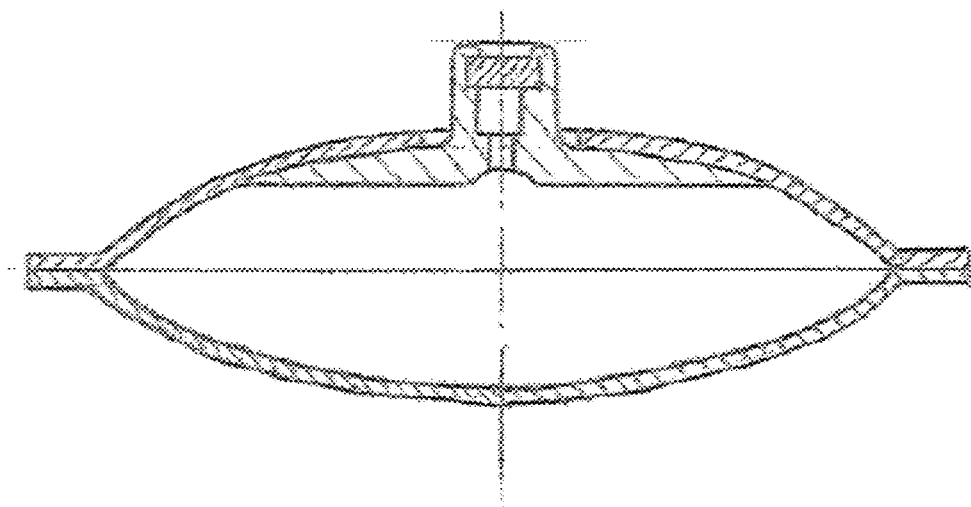
FIG. 1 shows a flexible container which may be filled with a filling apparatus and a filling method (described above).

REFERENCE SIGNS 5, 5', 105 first support element
6 first inner container compartment surface
7 circumferential area
10, 10', 110 second support element
110a circumferential surface of second support element
11 second inner container compartment surface
12 circumferential area
13 spacer structure
15, 15' container compartment
15a, 15b sections of container compartment
20 flexible container
21, 21a foil sheets
22 circumferential bonding area
30 fluidic connector
35 filling cannula assembly
36 cannula holder
37 cannula
70 hinge
113 spindle receiving cavity
150 distance setting assembly
152 drive unit
154 threaded spindle
158 guiding ring
200, 200' filling pump
205 drug reservoir
210, 210' pressure controller
212, 212' pressure transducer
214, 214' pressure evaluation unit
230 timer unit
250, 250' controller unit
260 volume curve
a displacement axis
d distance
e cannula moving direction
P neutral plane
V filling volume
t time

DETAILED DESCRIPTION

Embodiments of the present invention disclose devices and methods that allow simple and convenient filling of a flexible container with a defined drug amount while preventing overfilling. Advantageously, this defined filling volume is variable. In contrast to industrial filling processes, approaches such as gravimetric measurements, flow sensors or high precision filling pumps are not feasible under the circumstances of the drug container being self-filled by the patient. Therefore, defined and easy filling is a major problem to be solved in this context.

The above problem is solved based on the insight that the filling volume of a flexible container is correlated with its expansion upon being filled and its resulting shape, wherein the shape and expansion of the container are unique for a given volume. Accordingly, by mechanically limiting the expansion of the flexible container, the maximum filling volume of the flexible container may be defined.

The term 'maximum filling volume' refers to the desired filling volume of the flexible container at the end of the filling process.

In the following, the embodiments of the invention are mainly described in the framework of CSII therapy as a major field of application with the drug being a liquid insulin formulation. Other embodiments may, however, also be used in the context of other applications such as cancer therapy or pain therapy without requiring substantial modifications. For CSII therapy, a flexible container according to an embodiment may be designed for a filling volume of typically 1 ml to 5 ml, or 100 I.U. to 500 I.U. (International Units) of an insulin formulation having the well-established concentration U100.

In one aspect, embodiments of the invention are directed towards a system for ambulatory drug infusion over an extended time period, the system comprising an ambulatory infusion apparatus, the infusion apparatus comprising: a flexible container or a container coupler for fluidically coupling a flexible insulin container, a dosing unit in fluidic connection with the flexible container or a dosing unit coupler for fluidically coupling the flexible container and the dosing unit, an electronic controller unit configured to control operation of the dosing unit, and further comprising a filling apparatus for the flexible container, the filling apparatus comprising a hollow support structure defining a container compartment, the container compartment being adapted to receive, fully or in part, the flexible container, the support structure being adapted to limit the expansion of the flexible container by contacting the flexible container upon being filled, thus defining a maximum filling volume of the flexible container.

The flexible container is made of two sheets of an elastic foil sheets as disclosed, for example in the co-pending European patent application 08167548.0. Some characteristics of such flexible containers are dealt in more detail below.

The dosing unit may be, for example, a miniaturized volumetric piston pump as disclosed in the European patent application EP 1970677A1 or may be a micro membrane pump, a peristaltic pump, or the like. The dosing unit or its drug-contacting portions are single-use items and may be provided separate from or as integrated unit with the flexible container. Besides the flexible container, the dosing unit is adapted to fluidically couple to an infusion tubing having an infusion cannula or directly to an infusion cannula in case the infusion apparatus is designed to be directly attached to the patient's skin.

The flexible container, the dosing unit and/or the filling apparatus may comprise a degassing assembly such as an air permeable membrane in order to allow air bubbles to escape the system, thus preventing them from entering the flexible container when being filled and/or entering the dosing unit. Both the flexible container and the dosing unit, or its disposable components respectively, are preferably designed in one embodiment to be placed in corresponding components of a housing of the infusion apparatus or may be provided with housings of their own and may be coupled to the infusion apparatus.

The electronic controller unit is an, e.g., microcontroller-based, state-of-the-art electronic controller as substantially known from current ambulatory infusion apparatuses. The electronic controller controls operation of the dosing unit via an electrical actuator, such as a motor drive. The infusion apparatus further comprises additional components, such as a supervision circuitry, user interface, data interface, power supply, and the like.

The filling apparatus according to the invention allows filling the flexible container to a pre-defined maximum filling volume without having to meter the drug at its entry into the flexible container since the maximum filling volume of the flexible container is defined by the container compartment of the filling apparatus.

The support structure may be, for example, a substantially rigid plastic or metal grid or shells and may be produced, for example, by machining or injection molding. Advantageous and exemplary embodiments of the support structure are described below in greater detail. The support structure may be designed such that the whole flexible container fits into the container compartment. In some embodiments of the flexible container, however, only a portion of the flexible container stores the drug and expands upon being filled. In this case, only the drug-filled portion of the flexible container may fit into the drug compartment of the filling apparatus. The support structure enables access to a filling port of the flexible container, e.g., by an aperture in the support structure.

In some embodiments of the filling apparatus, the shape of the container compartment substantially corresponds to the shape of the flexible container after being filled. In case only a part of the flexible container fits into the filling apparatus, the shape of the container compartment may fit to that part of the drug container.

Designing the container compartment to have this shape results in a maximum contact area of the support structure on the one hand and the flexible container on the other hand when the flexible drug reservoir is filled. This is particular favorable as it best defines the shape and thus the filling volume of the flexible container. For this type of design, the maximum filling volume of the container is substantially equal to the volume of the container compartment minus the constant and often negligible material volume of the sheets making the flexible container body. In alternative embodiments, the container compartment has a different shape and may be, for example, cylindrical for manufacturing methods and manufacturing costs reasons. For this type of design, the volume of the container compartment is somewhat larger than the volume of the filled flexible container, resulting in the contact area of the flexible container and the support structure being somewhat reduced. Depending on the overall dimensions and the material properties of the flexible container material, in particular its elasticity and creeping characteristics, this may be acceptable. For this type of embodiment, the volume of peripheral sections of the container compartment volume that is not filled by the flexible container after filling is preferably substantially smaller as compared to the volume of the flexible container. In further alternative embodiments, the shape of the container compartment is substantially different from the shape of the flexible container in its filled state. For this type of embodiment, the flexible container is forced by the support structure into a shape which is different from the shape it would assume if being filled without the presence of the support structure.

In some embodiments, the filling apparatus comprises a positioning structure for positioning the flexible container with respect to the support structure and holding it in place. The positioning structure may for example comprise releasable clamps for axially clamping the flexible container along its circumferential bonding area. Alternatively, a number of holes may be provided in the circumferential bonding area of the flexible container which engages corresponding holing pins of the filling apparatus or vice versa. The positioning structure is preferably designed to hold the flexible container in a neutral plane. The neutral plane is a symmetry plane of the container compartment as described below in more detail. While holding the flexible container in place, the positioning structure is designed such that the flexible container is floating and/or shows some play when being filled in order to avoid or limit bracing of the flexible container and to allow the flexible container to smoothly fit the contour defined by the container compartment.

In some embodiments, the support structure of the filling apparatus comprises a first support element and a second support element, the first support element and the second support element defining a first inner container compartment surface and a second inner container compartment surface, the inner container compartment surfaces facing each other.

Those support elements may be, for example, disk-shaped and coaxially displaced with respect to each other along a displacement axis which is parallel or identical with the main direction of expansion. The container compartment surfaces defined by the disks may be flat or concave (when viewed from the container compartment inside) in order to correspond to the shape of the flexible container in its filled state. In case of the flexible container being made from circular sheets, the container compartment surfaces may have, for example, the shape of sphere segments or a parabolic shape or be free-forming surfaces. The first inner container compartment surface and the second inner container compartment surface are preferably mirror-symmetric with respect to each other.

The first support element and the second support element may further contact each other in, for example, a circumferential contacting zone. The contacting zone defines the neutral plane. The first inner container compartment surface and the second inner container compartment surface are symmetric to both sides of this plane. The first support element and the second support element may further, in combination, provide a positioning structure for the flexible container as described above.

Some embodiments of the filling apparatus, comprising a first and a second support element, further comprise a volume setting assembly, wherein operating the volume setting assembly displaces at least one of the first support element and the second support element with respect to the other support element along a displacement axis. For this type of embodiment, the maximum filling volume of the flexible container may be adjusted by adjusting, via the volume setting assembly, the volume of the container compartment of the filling apparatus.

The displacement axis is a common center axis and/or symmetry axis of the support elements and is parallel or identical with the main direction of expansion of the flexible container. Displacing either of the support elements results in a modification in the distance between the first inner container compartment surface and the second inner container compartment surface. The corresponding difference in the container compartment volume is proportional to the displacement. Therefore, the maximum filling volume of the flexible container may be adjusted by adjusting the displacement.

In some embodiments of the filling apparatus, and especially in embodiments having at least one displaceable support element as described above, the support elements are somewhat spaced from each other such that gap exists between the first inner container compartment surface and the second inner container compartment surface. A displacement of either of the support elements results in a modification in the gap width corresponding to the displacement. For flexible containers as may be used in the framework of insulin therapy, the gap width may be in typical range, of zero to, e.g., 4 mm. The maximum distance between the support elements along the direction of extension of the flexible container is typically about 1 cm or below for this type of application.

Accordingly, the flexible container may expand into the gap when being filled. This is uncritical as long as the gap width is sufficiently small. A large gap width may especially occur if a large filling volume range of the flexible container, and thus a large displacement range, is required. Therefore, the support elements may be connected by a gap compensation structure, such as a telescopic arrangement or a bellows in the gap area, the gap compensation structure making a circumferential wall of adjustable length. For such arrangements, the surface of the container compartment is substantially enclosed independent of the gap width, such that substantially the whole surface of the flexible container is in contact with the support structure when the flexible container volume is maximal.

In some embodiments, only one of the support elements is displaced when the volume setting assembly is operated. In alternative embodiments, both support elements are displaced about the same distance and in opposite directions. This is especially favorable to ensure symmetric expansion of the flexible container upon being filled independent of the displacement adjustment. An equivalent effect may be achieved by displacing one of the support elements and displacing the fixing structure into the opposite direction.

In some embodiments of the filling apparatus comprising a volume setting assembly, the volume setting assembly comprises an electrical actuator and a controller unit, the controller unit controlling operation of the electrical actuator.

The volume setting assembly may comprise a spindle drive, wherein a threaded spindle is in engagement with at least one of the support elements. The electrical actuator may be, e.g., a DC motor or a stepper motor. The spindle drive may further comprise sensor elements such as a rotary and/or linear encoder for providing feedback to the controller unit.

Additionally or alternatively, the spindle may be rotated manually for setting the maximum filling volume. For a manually operable volume setting assembly, a scale such as a ruler and/or micrometer scale are provided. Besides a spindle drive, further designs of both electrically operated as well as manual designs for realizing the linear displacement are known in the art and may be employed as well.

In some embodiments of the filling apparatus comprising a first support element and a second support element, the apparatus further comprises a replaceable spacer structure, the spacer structure being arranged between the first support element and the second support element, the spacer structure defining the maximum filling volume of the flexible container.

The spacer structure may have the shape of a hollow cylinder or ring, the length of which in the displacement direction defining the displacement between the first support element and the second support element. Alternatively, the spacer structure may be made by one or several bolts extending in the displacement direction, the length of the bolts defining the displacement between the first support element and the second support element. If the spacer structure shows a closed inner surface, it may further serve as gap compensation structure as described above. This type of embodiment is especially favorable if only a set of defined filling volumes of the flexible container is required rather than continuous adjustment. In the framework of diabetes therapy, for example, a set of three filling volumes, e.g. 100 I.U., 200 I.U. and 300 I.U. may be sufficient. A corresponding set of spacer structures for alternative use may accordingly be provided.

In some embodiments, the filling apparatus comprises a filling pump in order to allow the process of filling the flexible container to be especially convenient and fail-proof.

In some embodiments of the filling apparatus comprising a filling pump, the filling apparatus comprises a filling timer operatively coupled to the filling pump, the filling timer being adapted to control the filling pump to operate for a given filling time.

When a flexible container is filled, the pressure associated with the expansion causes a tensile stress of the elastic foil sheets of the flexible container. Since materials typically used for the flexible container tend to strain in a creeping way under the influence of tensile stress, thus increasing the filling volume of the flexible container in a creeping way. This undesired effect is especially likely to occur at the end of the filling process, when the further expansion of the flexible container is limited or prevented due to the flexible container walls contacting the support structure and the internal pressure of the flexible container is large. Creeping of the container walls is hard to control and may therefore result in a considerable variability of the filling volume. By operating a filling pump for a given and well defined filling time, this variability can be largely reduced. An appropriate filling time is typically in the range of 10 seconds to 2 minutes, and may be determined by simulation and/or routine experiments for a given design of the flexible container. The filling pump may be both electrically or manually operated.

For this type of embodiment, operating the filling pump for a given filling time with a given pressure is an additional means for controlling the creeping which occurs at the end of the filling process and thus reducing the variability of the maximum filling volume, while it is mainly defined by the support structure.

In some embodiments of the filling apparatus comprising a filling pump, the filling pump is a pressure pump, the pressure pump being adapted to fluidically couple to the flexible container and to a drug reservoir, the pressure pump being further adapted to force drug out of the drug reservoir and into the flexible container. The filling pump may be of any design known in the art for pumping small liquid amounts, such as a peristaltic pump, a membrane pump, a geared pump, or the like. The maximum filling volume and, thus, the liquid volume to be pumped is typically in a range of 1 ml to 5 ml.

In some alternative embodiments of the filling apparatus comprising a filling pump, the filling pump is an suction pump, the suction pump being fluidically coupled to the container compartment, the suction pump being adapted to suck air out of the container compartment, thus expanding the flexible container and sucking drug from a drug reservoir fluidically coupled to the flexible container into the flexible container.

This type of embodiment is especially advantageous in so far as the filling pump pumps air rather than drug. It does not come into contact with the drug and does therefore neither need to be sterile nor disposable. Furthermore, the fluidic connection is especially simple since the flexible container is fluidically connected only with the drug reservoir without the filling pump in between them. The fluidic connection of the suction pump with the container compartment may be permanent.

For this type of embodiment, the container compartment is preferably sealed to be air-tight during the filling process. This may be achieved by sealing elements known in the art, such as O-rings between the support elements. The support structure further comprises fluidic connectors and/or couplers for fluidically coupling the container compartment with the suction pump.

The drug reservoir from which the drug is supplied is typically a standard vial having a pierceable septum and comprises, for example, 10 ml or 1,000 I.U. of a liquid insulin formulation. The fluidic connection between the drug reservoir and the filling pump or the flexible container, respectively typically comprises a venting assembly as known in the art.

In some embodiments where the filling apparatus comprises a filling pump, the filling apparatus comprises a pressure controller, the pressure controller being adapted to control or limit the operational pressure of the filling pump. Besides the filling time, the filling pressure is a crucial parameter for filling a flexible container in a defined and reproducible manner. The pressure controller of this type of embodiment may especially comprise an electrical pressure transducer and a typically electronic pressure evaluation unit, the pressure evaluation controlling operation of the filling pump. Alternatively, the pressure controller may be a mechanical pressure controller or pressure limiting device as known in the art.

In some embodiments, the support structure of the filling apparatus is, at least in part, integral with a housing of the infusion apparatus. Providing a support structure integral with the housing of the infusion apparatus shows the advantages of reducing the number of single devices that have to be provided as well as the number of handling operations that have to be performed by the patient.

The infusion apparatus may comprise a container compartment which may be opened for replacing the flexible container and/or the dosing unit. In such an embodiment, the main body of the infusion apparatus housing serves as one of a first support element and a second support element, while a preferably present cap or closure serves as the other of the two support elements. For this type of embodiment, the empty flexible container may be inserted into the infusion apparatus and the container compartment may be closed before filling the flexible container. In order to allow different filling volumes, a set of different spacer elements as described above or a set of different closures or caps may be provided.

In some alternative embodiments, the filling apparatus is a dedicated apparatus separate from the infusion apparatus.

In some embodiments, the support structure of the filling apparatus is, at least in part, integral with a removable packaging of the flexible container. For this type of embodiment, the support structure may be made of cost-efficient plastic components, stiff foils, or the like and like the flexible container, is designed for single use. For this type of embodiment, the flexible container may be provided readily positioned in the container compartment of the filling apparatus. To allow different filling volumes, a variety of such assemblies may be provided. Alternatively, only a part of the support structure, in particular one of the support first or the second support element as described above, may be integral with the packaging of the flexible container. Other parts of the support structure, in particular the other of the first and the second support element, may be reusable and adjustable as described above.

According to a further aspect, the invention is directed towards a flexible container assembly, comprising:
a) a flexible container, the flexible container comprising a container body at least one wall of which is made by a sheet of an elastic foil and a fluidic connector for fluidically connecting the container, the flexible container expanding upon being filled,
b) a hollow support structure defining a container compartment, the flexible container being, at least in part, arranged in the container compartment, the support structure being adapted to limit the expansion of the flexible container by contacting the flexible container upon being filled, thus defining a maximum filling volume of the flexible container.

The flexible container may especially be a container having a container body made of two elastic foil sheets which are bonded in a circumferential area as described above and exemplary shown in FIG. 1.

Embodiments of a filling apparatus according to the present invention as described above and below constitute embodiments of a support structure of a container assembly according to this aspect of the invention.

According to a still further aspect, other embodiments of the invention are directed towards the use of a flexible container in or in combination with a system for ambulatory drug infusion as or in a container assembly as described above.

In the following, exemplary embodiments of a filling apparatus are described in greater detail with reference to the figures. Instead of a dedicated filling apparatus, the support structures may be used in a container assembly as described above.

Figure 2A:
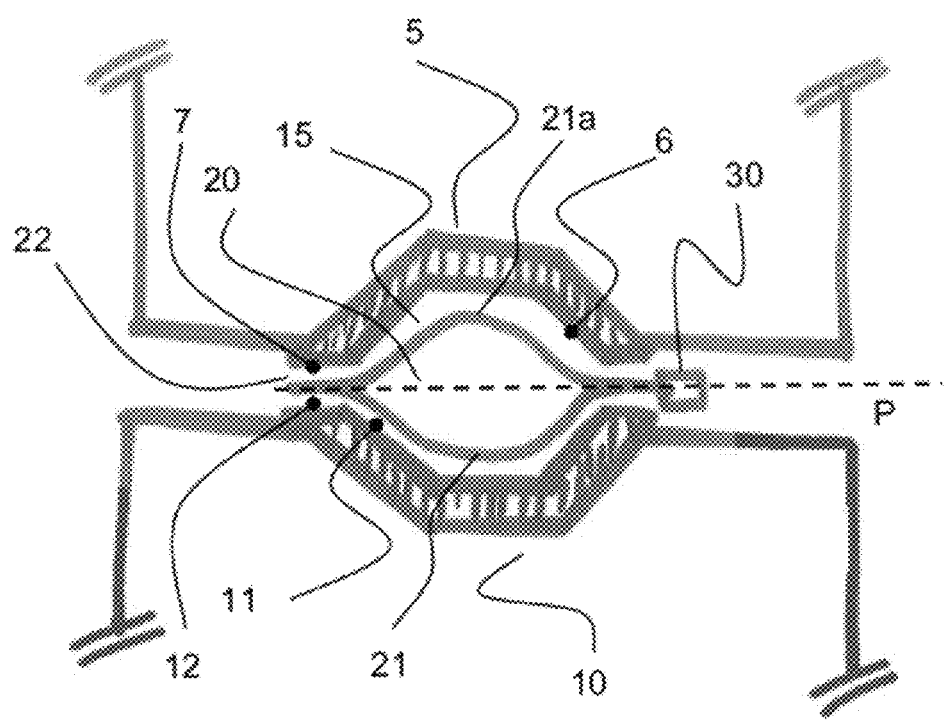
FIG. 2a schematically shows a cross sectional view of a filling apparatus according to an embodiment of the present invention.

FIG. 2a schematically shows a cross sectional view of an exemplary filling apparatus according to the present invention along with a flexible container.

The exemplary flexible container 20 is a container according to FIG. 1 as described above. An exemplary flexible container of this type is circular and essentially flat if it is empty and has a circular and "cushion-like" form in its filled state as described above.

The filling apparatus comprises a first support element 5 and a second support element 10, the support elements, in combination, making the support structure. The support elements are made of any substantially rigid material such as metal or plastics. The inner surface of the first support element 5 makes a first inner container compartment surface 6 and the inner surface 11 of the second support element 10 makes a second inner container compartment surface 11. A flexible container 20 which is placed in the metering cavity or drug receiving cavity 15 is clamped by the first support element 5 and the second support element 10 at its circumferential area 22. The circumferential areas 7, 12 of the first support element 5 and the second support element 10, respectively, form a fixing structure, fixing the flexible container 20 in the neutral plane P.

The exemplary flexible container 20 comprises or is coupled to a fluidic connector 30 at its circumference. However, the fluidic connector may alternatively be placed at any other position of the flexible container 20.

As long as the flexible container 20 is empty, it is essentially flat and rests in the neutral plane P. When it is filled by forcing drug via the fluidic connector 30 into it, it expands. When the foil sheets 21, 21a contact the first inner container compartment surface 6 and the second inner container compartment surface 11, respectively, the further expansion is limited. The shape of the first inner container compartment surface 6 and the second inner container compartment surface 11 are such that they correspond to the shape of the flexible container 20 in its filled state. The foil sheets 21, 21a will accordingly contact the inner container compartment surface 6 and 11, respectively. In this state, the filling volume of the flexible container 20 is substantially equal to the volume of the drug receiving cavity 15 and corresponds to the maximum filling volume.

In this exemplary embodiment, the first support element 5 and the second support element 10 are fixed in place with respect to each other.

Figure 2B:
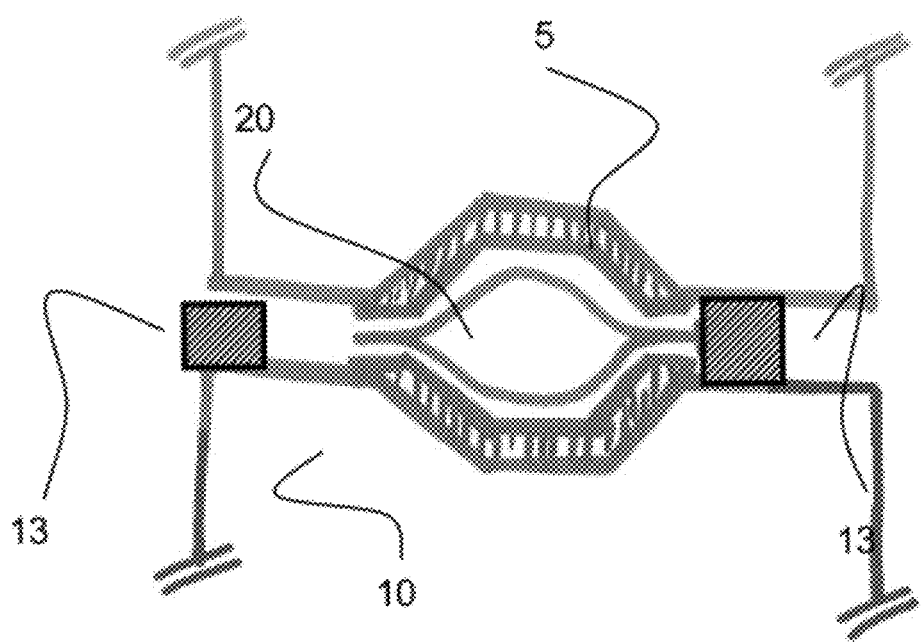
FIG. 2b schematically shows a cross sectional view of a filling apparatus according to another embodiment of the present invention.

FIG. 2b shows a filling apparatus which is very similar to the one shown in FIG. 2a except that a, for example ring-shaped, spacer structure 13 is additionally provided which may optionally be replaceable.

Besides a separate apparatus, the filling apparatus may be integral with the container packaging as well as in a container assembly as described above since only a small number of low-cost components is required.

Figure 3:
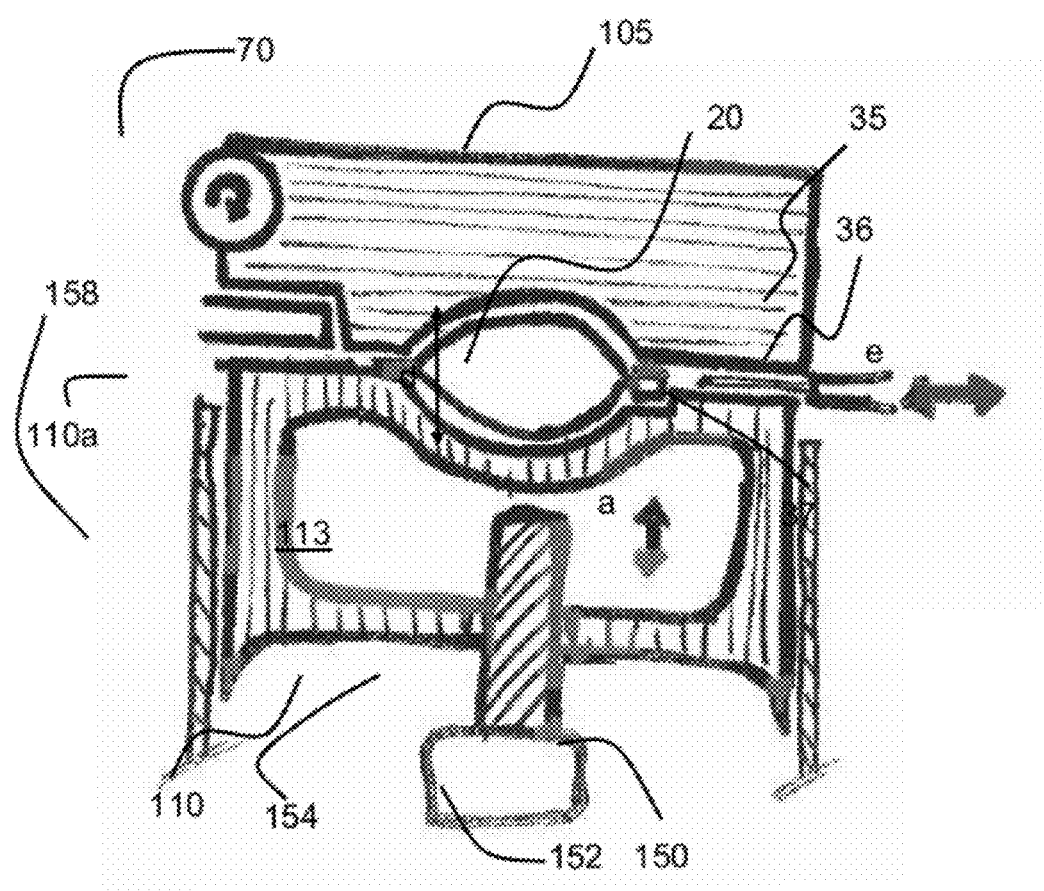
FIG. 3 schematically shows a cross sectional view of a filling apparatus according to still another embodiment of the present invention.

FIG. 3 shows a further exemplary filling apparatus in a view corresponding to FIG. 2a. This exemplary embodiment shows a number of improvements as compared to the previously described embodiment. Those improvements and additional features, however, may not be used only in this specific combination but also in connection with other embodiments.

The filling apparatus comprises a volume setting assembly 150. The volume setting assembly 150 comprises a drive unit 152 having a rotary drive, such as a DC motor or stepper motor, and an optional reduction gear and may further comprise an encoder for providing feedback. The volume setting assembly 150 further comprises a threaded spindle 154. The volume setting assembly 150 further comprises a circular guiding ring 158, the guiding ring 158 being in sliding axial engagement with the circumferential surface 110a of the second support element 110. The second support element 110 further comprises a threaded hole (not referenced) which is in threaded engagement with the spindle 154, the spindle 154 projecting into a spindle receiving cavity 113 of the second support element 110. An anti-rotation assembly (not shown) is further provided at the contact area of the guiding ring 158 and the circumferential surface 110a of the second support element 110.

Accordingly, operation of the drive unit 152 results in a linear displacement of the second support element 110 along axis a in alignment with the direction of main expansion of the flexible container. Displacement of the second support element 110 results in an adjustment of the distance d which may be measured between any two points of the first support element 105 and the second support element 110 along the displacement axis a. Adjusting the distance d is associated with a corresponding adjustment of the volume of the container compartment. The drive unit 152 is controlled by a preferably electronic controller unit (not shown in FIG. 3) according to the state of the art.

Alternatively to the set up shown in FIG. 3, further arrangements of the volume setting assembly may be employed. For example, instead of providing a drive unit 152, the spindle 154 may be designed to be rotated manually for adjusting the distance d. In such an embodiment, a manual readable scale, such as a micrometer scale, is preferably provided in addition. Such a scale preferably shows the resulting maximum flexible container volume rather than the distance d. In a further variation, the distance d may be adjusted by providing a set of spacer structures of different lengths which may be placed between the first support element 105 and the second support element 110. This type of arrangement allows an especially cost-efficient stepwise adjustment of the distance B and thus the maximum filling volume of the flexible container 20.

In the embodiment shown in FIG. 3, the first support element 105 is further removable by a pivoting movement. For this purpose, a rotary hinge 70 is provided. This allows easy and comfortable access to the container compartment for placing and removing the flexible container 20. In addition to the hinge 70, a fixing assembly (not shown) is preferably provided for fixing the first support element 105 and the second support element 110 with respect to each other when filling the flexible container 20. Alternatively, the first support element 105 may be slidable or fully removable.

In the embodiment shown in FIG. 3, the fluidic connector 30 comprises a pierceable septum (not visible in FIG. 3). A filling cannula assembly 35 is provided, comprising a cannula holder 36 and a cannula 37. The filling cannula assembly 35 is displaceable in a cannula moving direction e perpendicular to the septum of the fluidic connector 30 with the cannula being in the neutral plane. Displacement of the filling cannula assembly 35 is performed by an actuation assembly (not shown in FIG. 3). The actuation assembly may be manually or automatically operated and may especially be coupled to the first support element 105, such that the cannula 37 pierces the septum upon moving the first support element 105 into the closed position shown in FIG. 2 and is retracted upon removing the first support element 105. Alternatively, a separate manual or electrical actuator may be provided.

Figure 4:
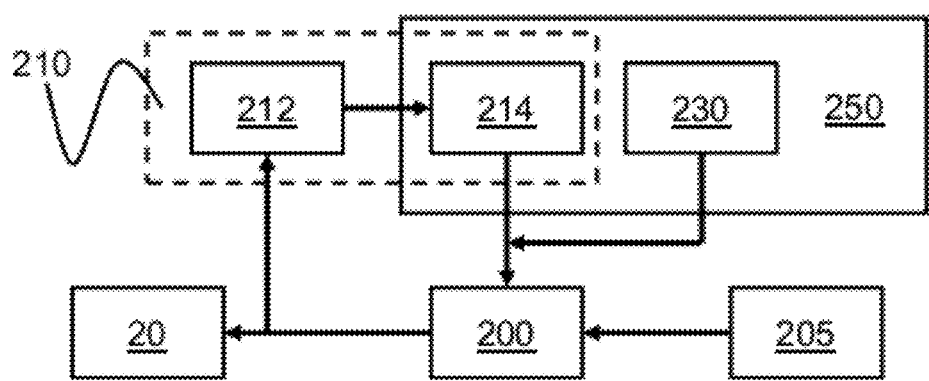
FIG. 4 shows a structural and functional view of another exemplary filling apparatus.

FIG. 4 schematically shows a structural and functional view of another embodiment of a filling apparatus according to the present invention. The mechanical structure of the shell (not shown in FIG. 3) may be according to FIG. 2, FIG. 3 or according to another design as given above in the general description of the invention.

The embodiment shown in FIG. 4 comprises a filling pump 200 and a controller unit 250. The filling pump 200 in one embodiment is a pressure pump and is arranged between the drug reservoir 205 and the flexible container 20. The filling pump 200 is controlled by the controller unit 250 which is realized based on state-of-the-art electronic circuitry. The exemplary filling apparatus further comprises a pressure controller 210, the main functional components of which are a pressure transducer 212 and a pressure evaluation unit 214. The pressure transducer 212 is fluidically arranged between the filling pump 200 and the flexible container 20, thus measuring the filling pressure. The pressure transducer 212 may be realized according to any state of the art design and be, for example, a capacitive or piezo resistive transducer. The pressure evaluation unit 214 is integral with the controller unit 250 and controls the filling pump 200 such that the filling pressure is substantially constant. It can be seen from FIG. 4 that the filling pump 200, the pressure transducer 212 and the pressure evaluation unit 214, in combination, make a closed-loop control structure. The controller design may be selected by a person skilled in the art based on the system properties and in particular the characteristics of the filling pump 200 and work, for example, as PI-controller or PID-controller. The controller unit 250 further comprises a filling timer 230. The filling timer 230 controls the filling pump 200 to operate for a given filling time.

In the embodiments shown in FIG. 2 and FIG. 3, any manually operated over-pressure device, such as a syringe, may be used for forcing drug into the flexible container 20. As described above, however, this results in some undesired variability of the filling volume. By filling the flexible container 20 with a defined and substantially constant filling pressure for a defined filling time according to the exemplary embodiment shown in FIG. 4, this variability is largely avoided while the maximum filling volume is mainly defined by the container compartment.

Figure 5:
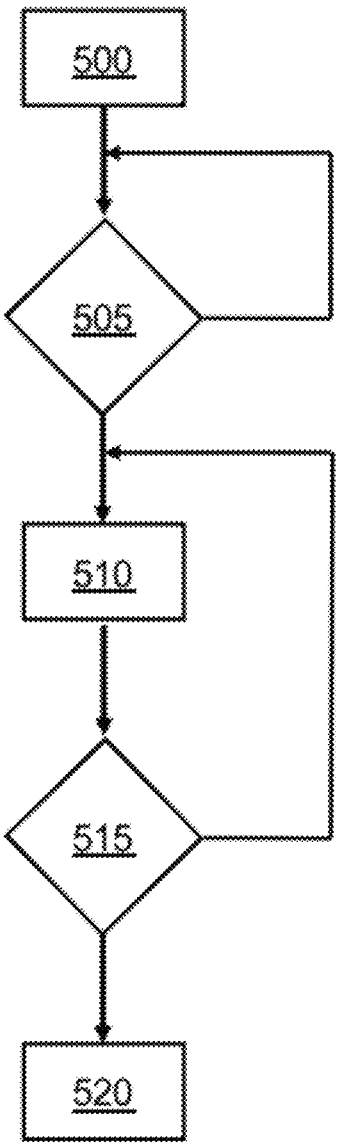
FIG. 5 shows the control flow of the major steps for filling a flexible container with a filling apparatus according to FIG. 4.

FIG. 5 schematically shows the control flow of the filling process as controlled by the controller unit 250. In step 500, the filling pump 200 as well as the filling timer 230 are started. In step 505, it is determined if the desired target pressure has been assumed. As long as this is not the case, the filling pump 200 is controlled to further increase the filling pressure. In step 510, the filling pump is controlled to maintain the filling pressure. In this state, the flexible container 20 contacts the inner surfaces of the support structure and has largely assumed its maximum filling volume. However, the filling volume still increases due to the creeping strain of the foil sheets. In step 515, it is checked if the filling pump has been operated for the given filling time. If the filling time is not assumed, the steps 510 and 515 are further carried out as a loop and the filling pump 200 is further controlled to maintain the target filling pressure. At the end of the given filling time, the filling pump 200 is stopped in step 520. Here it is assumed, that the time for assuming the target filling pressure is short as compared to the filling time. If this is not the case, the filling timer may be started only after the target filling pressure has been assumed.

Figure 6:
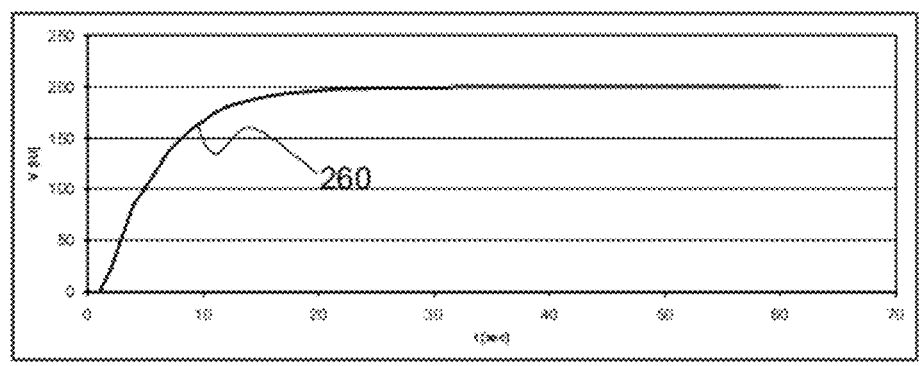
FIG. 6 shows the filling volume of a flexible container as a function of time t for a filling apparatus according to FIG. 4.

FIG. 6 exemplary shows the filling volume of a flexible container when filled with a filling apparatus according to FIG. 4 and a filling process according to FIG. 5 at a target filling pressure of 200 mbar. It can be seen that the flexible container is largely filled within the first 10 seconds, but the filling volume further continues for a substantially longer time. A filling time of 60 sec. and a filling pressure of 200 mbar as shown in FIG. 6 are typical parameters for the intended application. However, other values may be used too. In particular, the filling pressure may be somewhat lower and be, for example, about 100 mbar.

Figure 7:
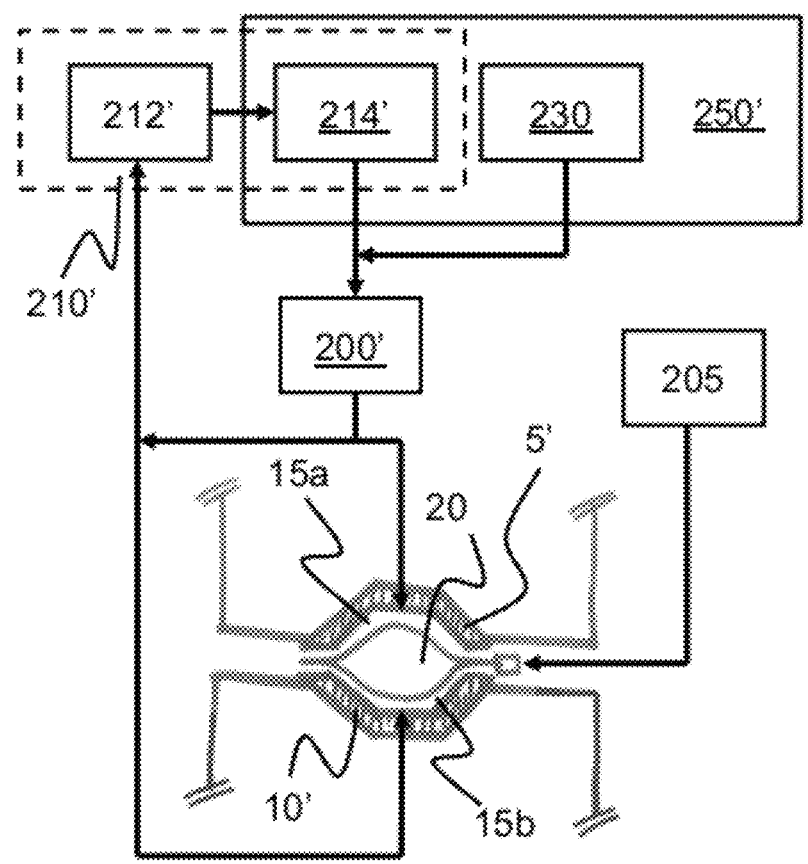
FIG. 7 shows a structural and functional view of another exemplary filling apparatus.

FIG. 7 schematically shows a filling apparatus according to another exemplary embodiment of the invention. While the mechanical structure is similar to the one shown in FIG. 2, it may also be a structure according to FIG. 3 or a further embodiment as described above.

The filling apparatus shown in FIG. 7 is similar to the filling apparatus shown in FIG. 4. However, the filling pump 200' in this alternate embodiment is a suction pump, the filling pump 200' being fluidically coupled to the container compartment 15' and being adapted the generate a negative pressure in the container compartment. The contact area between the first support element and the second support element (not referenced) as well as the fluidic connection to the drug reservoir 205 (not referenced) are designed to be sealed to ensure tightness with respect to gas and in particular air. For this purpose, sealing components (not shown) such as O-rings may be used. The sealing components may be integral with the first support element, the second support element and/or the flexible container 20. The filling pump 200' is fluidically connected to both sections 15a, 15b of the container compartment on both sides of the flexible container 20. The flexible container 20 acts as sealing or barrier. Therefore, both the first support element 5' and the second support element 10' comprise corresponding fluidic connector. Only connecting one of the first support elements 5' or 10' to the filling pump 200' is also possible but results in a less favorable unsymmetrical under pressure in the container compartment.

The operation of the pressure transducer 212', the pressure evaluation unit 214' and the controller unit 250' is substantially identical to the exemplary embodiment described above with reference to FIG. 3. However, they are designed for under-pressure rather than over-pressure with reference to the ambient pressure.

The drug reservoir 205 is directly fluidically coupled to the flexible container 20 in this embodiment.

The filling process may be carried out in an equivalent way to the process represented by FIG. 5.

In all exemplary embodiments, the mechanical structure, in particular the shells may be integral fully or partly with the housing of the infusion apparatus. Further components, in particular, the controller unit 250, 250' may be integral with the infusion apparatus controller unit.

What is claimed is:

1. System for ambulatory drug infusion of a liquid drug over an extended time period, the system comprising:
an ambulatory infusion apparatus, in which the infusion apparatus comprises:
a flexible container comprising a rigid portion and a flexible portion that are coupled to one another and define a fluidic reservoir for containing the liquid drug, wherein the rigid portion of the flexible container is coupled to a top or cover made from a flexible foil sheet and a fluidic connector, the flexible container defining a filling volume therein for receiving the liquid drug, and the fluidic connector for fluidically connecting and filling the filling volume of the flexible container with the liquid drug,
a dosing unit in fluidic connection with the filling volume of the flexible container via the fluidic connector, and
an electronic controller unit configured to control operation of the dosing unit; and
a filling apparatus for the flexible container, in which the filling apparatus comprises a hollow support structure defining a container compartment, the container compartment being adapted to receive, fully or in part, the flexible container, and the hollow support structure further comprising a first support element and a second support element, the first support element and the second support element being adapted to limit expansion of the flexible container by contacting the flexible foil sheet and the partly rigid container body of the flexible container upon the filling volume of the flexible container being filled by the dosing unit with the liquid drug to a maximum filling volume, wherein a spacer structure is coupled to the first support element and the second support element, the spacer structure adjustably defining a displacement distance between the first support element and the second support element that adjustably defines the maximum filling volume of the flexible container.

2. System according to claim 1, wherein the shape of the container compartment of the filling apparatus substantially corresponds to the shape of the flexible container after being filled.

3. System according to claim 1, wherein the filling apparatus comprises a positioning structure for fixing the flexible container with respect to the hollow support structure.

4. System according to claim 1, wherein the first support element and the second support element define a first inner container compartment surface and a second inner container compartment surface, the container compartment surfaces facing each other.

5. System according to claim 4, wherein the filling apparatus comprises a volume setting assembly, wherein operating the volume setting assembly displaces at least one of the first support element and the second support element with respect to the other support element along a displacement axis.

6. System according to claim 5, wherein the volume setting assembly of the filling apparatus comprises an electrical actuator and a controller unit, the controller unit controlling operation of the electrical actuator.

7. System according to claim 1, wherein the filling apparatus comprises a filling pump.

8. System according to claim 7, wherein the filling apparatus comprises a filling timer operatively coupled to the filling pump, the filling timer being adapted to control the filling pump to operate for a given filling time.

9. System according to claim 7, wherein the filling pump of the filling apparatus is an pressure pump, the filling pump being adapted to fluidically couple to the flexible container and to a drug reservoir, the filling pump being adapted to force drug out of the drug reservoir and into the flexible container.

10. System according to claim 7, wherein the hollow support structure comprises a fluid-tight container compartment and the filling pump of the filling apparatus is a suction pump, the filling pump being fluidically coupled to the container compartment, the filling pump being adapted to suck air out of the container compartment, thus expanding the flexible container and sucking drug from a drug reservoir fluidically coupled to the flexible container into the flexible container.

11. System according to claim 7, wherein the filling apparatus comprises a pressure controller, the pressure controller being adapted to control or limit the operational pressure of the filling pump.

12. System according to claim 1, wherein the hollow support structure of the filling apparatus is, at least in part, integral with a housing of the infusion apparatus.

13. System according to claim 1, wherein the hollow support structure of the filling apparatus is, at least in part, integral with a removable packaging of the flexible container.

14. Container assembly, comprising:
  a flexible container comprising a rigid portion and a flexible portion that are coupled to one another and define a fluidic reservoir for containing a liquid drug, wherein the rigid portion of the flexible container is coupled to a sheet of an elastic foil and defines a filling volume therein for receiving the liquid drug and a fluidic connector for fluidically connecting and filling the filling volume of the flexible container with the liquid drug, the flexible container expanding upon being filled; and
  a hollow support structure defining a container compartment, the flexible container being, at least in part, arranged in the container compartment, the hollow support structure further comprising a first support element and a second support element, the first support element and the second support element being adapted to limit the expansion of the flexible container by contacting the partly rigid container body and the sheet of the elastic foil of the flexible container upon the filling volume of the flexible container being filled via the fluidic connector to a maximum filling volume, wherein a spacer structure is coupled to the first support element and the second support element, the spacer structure adjustably defining a displacement distance between the first support element and the second support element that adjustably defines the maximum filling volume of the flexible container.

15. A method of preventing overfilling a flexible container with a defined drug amount comprising utilizing the flexible container in a container assembly according to claim 14.

16. System according to claim 8, wherein the filling pump of the filling apparatus is an pressure pump, the filling pump being adapted to fluidically couple to the flexible container and to a drug reservoir, the filling pump being adapted to force drug out of the drug reservoir and into the flexible container.

17. System according to claim 8, wherein the hollow support structure comprises a fluid-tight container compartment and the filling pump of the filling apparatus is a suction pump, the filling pump being fluidically coupled to the container compartment, the filling pump being adapted to suck air out of the container compartment, thus expanding the flexible container and sucking drug from a drug reservoir fluidically coupled to the flexible container into the flexible container.

18. System according to claim 10, wherein the filling apparatus comprises a pressure controller, the pressure controller being adapted to control or limit the operational pressure of the filling pump.

19. System according to claim 11, wherein the hollow support structure of the filling apparatus is, at least in part, integral with a removable packaging of the flexible container.

20. A method of preventing overfilling a flexible container with a defined drug amount comprising utilizing the flexible container in or in combination with a system according to claim 1.

* * * * *